United States Patent
Ourliac et al.

(10) Patent No.: US 11,592,430 B2
(45) Date of Patent: Feb. 28, 2023

(54) METHOD FOR ESTIMATING A COMBUSTION CHARACTERISTIC OF A GAS THAT MAY CONTAIN DIHYDROGEN

(71) Applicant: ENGIE, Courbevoie (FR)

(72) Inventors: Mathieu Ourliac, Saint Soupplets (FR); Sandra Capela, Pantin (FR); Laurent Lantoine, Conflans Sainte Honorine (FR); Naushad Manjoo, Eaubonne (FR)

(73) Assignee: ENGIE, Courbevoie (FR)

( * ) Notice: Subject to any disclaimer, the term of this patent is extended or adjusted under 35 U.S.C. 154(b) by 795 days.

(21) Appl. No.: 16/474,694

(22) PCT Filed: Dec. 15, 2017

(86) PCT No.: PCT/FR2017/053613
§ 371 (c)(1),
(2) Date: Jun. 28, 2019

(87) PCT Pub. No.: WO2018/122490
PCT Pub. Date: Jul. 5, 2018

(65) Prior Publication Data
US 2020/0232962 A1 Jul. 23, 2020

(30) Foreign Application Priority Data
Dec. 28, 2016 (FR) ......................... 1663468

(51) Int. Cl.
*G01N 33/22* (2006.01)
*G01N 25/22* (2006.01)
(52) U.S. Cl.
CPC ........... *G01N 33/225* (2013.01); *G01N 25/22* (2013.01)
(58) Field of Classification Search
CPC ............................. G01N 25/22; G01N 33/225
See application file for complete search history.

(56) References Cited

U.S. PATENT DOCUMENTS

| 5,122,746 A | 6/1992 | King et al. |
| 2004/0062290 A1 | 4/2004 | Cordier et al. |

(Continued)

FOREIGN PATENT DOCUMENTS

| CN | 104736680 A | 6/2015 |
| CN | 105807027 A | 7/2016 |

(Continued)

OTHER PUBLICATIONS

International Search Report dated May 4, 2018 in connection with International Patent Application No. PCT/FR2017/053613, 5 pages.

(Continued)

*Primary Examiner* — Victoria H Lynch

(57) ABSTRACT

A method is provided for estimating at least one combustion characteristic of a fuel gas belonging to a family of fuel gases, where the at least one characteristic includes at least one of a Wobbe index or a higher heating value. The method includes measuring at least two flow properties of the fuel gas and measuring a dihydrogen content $X_{H_2}$ contained in the fuel gas. The method also includes estimating the at least one characteristic $$\Xi_{\frac{GN}{H2}}$$

using an empirical affine relationship of $$\Xi_{\frac{GN}{H2}} = \alpha + \beta \cdot Y + \gamma \cdot X_{H_2}.$$

Here, $\alpha$, $\beta$, and $\gamma$ are coefficients predetermined for the family of fuel gases, and Y is a variable representative of (Continued)

physical properties of the fuel gas prepared from the measurements of the at least two flow properties of the fuel gas.

20 Claims, 5 Drawing Sheets

(56) References Cited

U.S. PATENT DOCUMENTS

| 2010/0043528 | A1 | 2/2010 | Brothier et al. |
| 2011/0215247 | A1 | 9/2011 | Kastner |

FOREIGN PATENT DOCUMENTS

| CN | 106096763 | A | 11/2016 |
| DE | 102008029553 | B3 | 11/2009 |
| EP | 2679659 | B1 | 8/2016 |
| JP | S53129990 | U | 10/1978 |
| JP | 2010-515038 | A | 5/2010 |

OTHER PUBLICATIONS

Written Opinion of the International Searching Authority dated May 4, 2018 in connection with International Patent Application No. PCT/FR2017/053613, 12 pages.

Notification of Reasons for Refusal dated Sep. 7, 2021 in connection with Japanese Patent Application No. 2019-535340, 12 pages.

First Office Action dated Jun. 24, 2021 in connection with Chinese Patent Application No. 201780086457.0, 11 pages.

Dudiac et al., "Computational Fluid Dynamics along the Energy Value Chain: From Natural Gas processing to Industrial End-Use," Science Direct, Energy Procedia, vol. 143, Jul. 2017, 8 pages.

GB/T 11062-2014, ICS 75.060, E 24, "Natural gas—Calculation of calorific values, density, relative density and Wobbe index," Dec. 2014, 33 pages.

Indian Standard—Natural Gas—Calculation of Calorific Values, Density, Relative Density and Wobbe Index From Composition, ICS 75.050, IS 14504:1998, ISO 6976: 1995 (Reaffirmed 2003), Bureau of Indian Standards, Jan. 1998, 51 pages.

Notice of Office Action dated Feb. 22, 2022 in connection with Korean Patent Application No. 10-2019-7020867, 11 pages.

METHOD FOR ESTIMATING A COMBUSTION CHARACTERISTIC OF A GAS THAT MAY CONTAIN DIHYDROGEN

CROSS-REFERENCE TO RELATED APPLICATIONS AND PRIORITY CLAIM

This application claims priority under 35 U.S.C. § 365 to International Patent Application No. PCT/FR2017/053613 filed on Dec. 15, 2017, which claims priority to French Patent Application No. 1663468 filed on Dec. 28, 2016. Both of these applications are hereby incorporated by reference in their entirety.

BACKGROUND OF THE INVENTION

The invention relates to the general field of estimating combustion characteristics of a fuel gas forming part of a family of fuel gases, said at least one characteristic being the Wobbe index or the higher heating value.

A particular application for the invention lies in estimating combustion characteristics of a fuel gas containing dihydrogen, e.g. a fuel gas containing a quantity of dihydrogen lying in a range 0% to 20% by volume.

The use of renewable energy sources sometimes requires the use of means for storing energy, since such renewable sources may operate in a manner that is intermittent and de-correlated with energy requirements. This applies in particular with photovoltaic energy production or when producing electricity by means of wind turbines.

Proposals have been made to use the dihydrogen that is obtained by electrolyzing water as means for storing energy coming from renewable energy sources.

The dihydrogen as generated in this way can subsequently be stored in storages, e.g. underground, or it can also be injected into a natural gas distribution network. The gas that is obtained may thus contain dihydrogen in the range 0% to 20%.

The Wobbe index (in kilowatt hours per normal cubic meter ($kWh/Nm^3$)), which is the ratio of the heating value of a fuel gas over the square root of its density, and the higher heating value (in $kWh/Nm^3$) are the two main characteristic magnitudes of the fuel that have an influence on the combustion settings of gas burners, whether for home use or for industrial use.

Depending on the type of application for the gas, and on the measurement means used (whether or not flow rate is measured by suction-generating means) it is one or the other of these two parameters that is taken into consideration.

By way of example, for an injector fed at a constant feed pressure (e.g. a cooktop or a ribbon burner), the power delivered depends on the pressure, on the through section of the injector, on the head loss, and on the Wobbe index of the fuel.

For applications where a mass or volume flow meter is available, the power delivered depends on the measured flow and on the heating value.

Specifically, the heat delivered by a burner is proportional either to the Wobbe index, or to the higher heating value (HHV). Likewise, for hydrogen-free natural gases as distributed in Europe, the quantity of air needed to obtain stoichiometric combustion depends on one or the other of these characteristics of the fuel gas.

It should be observed that the European network for transporting and distributing natural gas is becoming more and more meshed and it is fed by a variety of supply sources, so the characteristics of the natural gas (Wobbe index and HHV, among others) can thus vary over time in non-negligible manner (±5% or even more), at any given point in the network.

With that in mind, industrial processes such as those performed in the glassmaking, ceramic, electricity production, lime, and metallurgy industries are sensitive to these variations. As a result, in order to optimize combustion, it is necessary to make use of specific solutions for regulating combustion. In order to perform regulation of this type, it is possible to measure the Wobbe index or the higher heating value.

With natural gas, there exist technological solutions for measuring these parameters that are simple, robust, and accurate. However such solutions are lacking when dihydrogen is present in the fuel. Error in measuring these parameters increases greatly once the volume of dihydrogen exceeds 1%, and there is no guarantee that the measurements are repeatable.

Furthermore, industrial equipment, and even domestic equipment, can be sensitive to adding dihydrogen, even in very small proportions.

As a result, there exists a need for novel measurement apparatuses capable of quantifying on a continuous basis the major combustion parameters of these novel fuels: not only for sensitive uses such as glassmaking or metallurgical processes, but also so as to enable network operators to manage locally the combustion characteristics of gas fuels delivered to users.

Methods have been proposed for measuring or estimating the Wobbe index and the heating value.

In particular there are four families of apparatuses that can be used for measuring the Wobbe index and/or the heating value of natural gas, possibly including a non-zero proportion of dihydrogen:

calorimetry (for heating value): Measurement involves burning a controlled quantity of gas.

Thereafter, the energy given off is quantified by the input/output temperature difference across a (gas or water) heat exchanger. Accuracy is of the order of 10% (i.e. 1.1 $kWh/Nm^3$) but each measurement takes about 10 minutes (min). That technology is being abandoned, little by little.

Combustion measurement (for the Wobbe index): measurement involves combustion of an air/gas mixture. The oxygen content in the combustion products is measured by a zirconia probe. The residual oxygen content is correlated with the combustibility index, which is itself correlated, for natural gases, with the Wobbe index. This type of apparatus costs about €15,000. This type of equipment operates with mixtures having a low dihydrogen content. (for dihydrogen contents greater than 5% by volume, the Wobbe index is no longer linearly proportional to the combustibility index). The drawback of this technology is low accuracy, of the order of 5% (i.e. 0.75 $kWh/Nm^3$) and considerable maintenance (ageing due to the high temperatures of the oven in which combustion of the mixture takes place).

Gas phase chromatography (for the Wobbe index and for the heating value): This technique serves to separate molecules from a gas mixture. The Wobbe index and the heating value can then be calculated on the basis of knowledge of the composition of the gas. For high-power fuel burning equipment (e.g. gas turbines), gas phase chromatography has generally replaced calorimetry and combustion measurement. The accuracy of these measurement apparatuses is better, of the order of 0.5% (i.e. 0.08 $kWh/Nm^3$ for the Wobbe index). This type of equipment can also operate with mixtures of natural gas and of dihydrogen, providing the equipment is fitted with a specific sensor capable of separating out the dihydrogen molecule. The major drawback of gas phase chromatography is cost, even when recent improvements are taken into account (cost price may lie in the range €20,000-€50,000). Furthermore, even in the best of circumstances, the response time of gas phase chromatography equipment is of the order of one minute. There can therefore be a mismatch between the gas that is measured and the gas that is actually being used by the fuel burning equipment (e.g. a burner).

Correlation apparatuses (for the Wobbe index or for the higher heating value): One or more physical magnitudes correlated with the Wobbe index or with the higher heating value is/are measured in such apparatuses. A correlation, performed by a computer, is then used to estimate the Wobbe index or the HHV. This type of apparatus makes it possible to obtain accuracy of up to 1% for natural gases of the kind distributed in Europe. The advantages of this type of technology are speed of response (instantaneous), cost (in the range €10,000-€20,000), robustness, and reduced maintenance. Nevertheless, the apparatuses on the market do not operate with mixtures of natural gas and dihydrogen. Once a real natural gas (not comprising pure methane) includes dihydrogen present at a few percent by volume, error increases dramatically.

The state of the prior art includes Document EP 1 346 215, which describes apparatus for measuring the Wobbe index by correlation.

Also known is Document U.S. Pat. No. 4,384,792, which describes apparatus for measuring and regulating the Wobbe index of a gas fuel by correlations, and regulating the Wobbe index.

Also known is Document U.S. Pat. No. 6,244,097, which discloses an apparatus for measuring the heating value of a gas fuel by correlations.

Finally, known Document DE 4 118 781 discloses an apparatus for measuring the heating value and the Wobbe index of a gas fuel by correlations.

The solutions disclosed in those documents present the drawbacks of correlation apparatuses. In particular, they are not suitable for use once the fuel gas under study includes dihydrogen, since their accuracy is too low.

Furthermore, and as mentioned above, other apparatuses that are capable of operating with mixtures of natural gas and dihydrogen are particularly expensive, which limits their applications to high-power equipment of the kind that might be installed in major industrial groups.

The invention seeks in particular to mitigate at least some of those drawbacks.

OBJECT AND SUMMARY OF THE INVENTION

The present invention satisfies this need by proposing a method of estimating at least one combustion characteristic of a fuel gas belonging to a family of fuel gases, said at least one characteristic being the Wobbe index or the higher heating value, the method comprising:

measuring at least two flow properties of said fuel gas;

measuring the dihydrogen content $X_{H_2}$ contained in said fuel gas;

said at least one characteristic $$\Xi_{\frac{GN}{H2}}$$

being estimated by means of the following empirical affine relationship:

$$\Xi_{\frac{GN}{H2}} = \alpha + \beta \cdot Y + \gamma \cdot X_{H_2}$$

where:

$\alpha$, $\beta$, and $\gamma$ are coefficients predetermined for the family of fuel gases; and Y is a variable representative of physical properties of said fuel gas prepared from said measured values of said at least two flow properties of said fuel gas.

This method thus relates to a correlation type procedure, and this method can thus be implemented simply and inexpensively, and this method enables results to be obtained very quickly.

The invention takes account of the dihydrogen content in the fuel gas, unlike prior art methods.

It may be observed that the invention is applicable to fuel gases having a dihydrogen volume content in the range 0% to 20%.

The inventors have observed that it is possible to use an empirical affine relationship of the same form both for estimating the higher heating value and the Wobbe index.

By way of indication, various different flow properties of the fuel gas can be measured, depending on whether it is a higher heating value or a Wobbe index that is being measured. In other words, the variable Y may have a form that differs depending on whether it is a higher heating value or a Wobbe index that is being measured.

Also, the coefficients $\alpha$, $\beta$, and $\gamma$ need not be constant and they may differ depending on whether a higher heating value or a Wobbe index is being measured.

It should also be observed that the flow properties of the fuel gas are properties measured in flow means and that they may be selected from the group comprising: flow rate, temperature, or indeed pressure.

The variable Y represents physical properties of the gas. By way of indication, the variable Y may be associated with one or more physical properties such as the viscosity of the fuel gas, its specific heat capacity (per unit weight), or indeed its density. Saying that the variable Y represents or is associated with these physical properties means that it can be written in the form of a mathematical function associating these physical properties. The variable Y may be written both in the form of a mathematical function associating the physical properties, and also in the form of a mathematical function associating the flow properties of the fuel gas, since these properties are used for preparing the variable Y. Specifically, for certain types of flow property measurement, it is possible to associate a plurality of such measurements with physical properties of the fuel gas of the flow.

Thus, by using the notation:

$U_{mes,1}$ for the measurement of the flow property $U_1$, $U_{mes,2}$ for the measurement of the flow property $U_2$; and $U_{mes,3}$ for the measurement of the flow property $U_3$, this gives:

$$Y = f(U_{mes,1}; U_{mes,2}; U_{mes,1})$$

In a particular implementation, the coefficients α, β, and γ are coefficients read from a chart having as input the measured value for the dihydrogen content $X_{H_2}$ and delivering as output said coefficients α, β, and γ.

This makes it possible to obtain an even more accurate estimate of the characteristic being estimated. In a particular implementation, said chart associates said coefficients α, β, and γ with value ranges for the dihydrogen content $X_{H_2}$ having a width of 1%.

In other words, the chart presents granularity of the order of 1%.

The inventors of the present invention have observed that this enables satisfactory accuracy to be obtained and to do so with a level of complexity that is acceptable.

In a particular implementation, the values of said coefficients α, β, and γ are obtained from a dataset relating to known gases of said family of fuel gases for which the value of Y and the combustion characteristics that are representative of said physical properties are known.

The term "known gases" is used to cover gases of composition that is known, e.g. gases for which the proportions of the various components of determined chemical natures are known. The person skilled in the art knows how to determine the combustion characteristics of such gases, and in particular can make use of known gases that contain a non-zero dihydrogen quantity.

In a particular implementation, the method comprises randomly generating combustion characteristics and values for Y that are representative of physical properties from said dataset relating to known gases of said family of fuel gases.

In a particular implementation, the Wobbe index and the higher heating value are estimated by means of two empirical affine relationships.

It is thus possible to estimate both of these combustion characteristics, in a single implementation of the method.

In a particular implementation, the method further comprises estimating the density of said fuel gas from the estimated Wobbe index and from the estimated higher heating value.

In a particular implementation, the method comprises regulating the combustion characteristic of the fuel gas or regulating the combustion characteristic of a fuel gas and an estimated stoichiometric volume of air or an estimated combustibility index corresponding to said estimated characteristic.

In a particular implementation, said at least one combustion characteristic of the fuel gas comprises the Wobbe index $$IW_{\frac{GN}{H2}};$$

and said measurement of at least two flow properties of said fuel gas includes measuring a mass flow rate of the fuel gas in sonic flow (i.e. at a speed greater than or equal to the speed of sound) through a fluid flow constriction (e.g. an orifice or a micro-nozzle), the measurement being taken at an absolute pressure measured upstream from the constriction and at an absolute temperature measured upstream from the constriction;

the method further comprising a calibration procedure during which a measurement is taken of a mass flow rate of a reference gas (e.g. methane) in sonic flow through said fluid flow constriction, at a reference absolute pressure measured upstream from the constriction and at a reference absolute temperature measured upstream from the constriction;

the empirical affine relationship used for estimating the Wobbe index $$IW_{\frac{GN}{H2}}$$

then being written:

$$IW_{\frac{GN}{H2}} = D + E \cdot Y + F \cdot X_{H_2}$$

with:

$$Y = \frac{Q_{mes,2}}{Q_{ref}} \cdot \frac{P_{ref}}{P_{mes}} \cdot \sqrt{\frac{T_{ref}}{T_{mes}}}$$

where:
$Q_{mes,2}$ is the measured mass flow rate of the fuel gas;
$P_{mes}$ is the measured absolute pressure of the fuel gas;
$T_{mes}$ is the measured absolute temperature of the fuel gas;
$Q_{ref}$ is the measured mass flow rate of the reference gas;
$P_{ref}$ is the measured absolute pressure of the reference gas; and
$T_{ref}$ is the measured absolute temperature of the reference gas; and
D, E, and F are predetermined coefficients for the fuel gas family and correspond respectively to the coefficients α, β, and γ.

In a particular implementation, the Wobbe index of said fuel gas is estimated, and the method further comprises measuring the density of said fuel gas and estimating the higher heating value from the estimated Wobbe index and from the measured gas density.

In a particular implementation, said at least one combustion characteristic of the fuel gas comprises the higher heating value $$HHV_{\frac{GN}{H2}},$$

and said measurement of at least two flow properties of said fuel gas comprises:
  measuring the mass flow rate of said fuel gas in laminar flow through an apparatus giving rise to a pressure drop, the measurement depending on the viscosity of the fuel gas and on the viscosity of a reference gas (e.g. methane); and
  measuring, downstream from said apparatus giving rise to a pressure drop, the mass flow rate of said fuel gas by means of a thermal mass flow meter, the measurement depending on the specific heat capacity of the fuel gas and on the heat capacity of a reference gas;
  the empirical affine relationship used for estimating the higher heating value $$HHV_{\frac{GN}{H2}}$$

then being written:

$$HHV_{\frac{GN}{H2}} = A + B \cdot Z + C \cdot X_{H_2}$$

with:

$$Z = \frac{Q_{mes,1}}{Q_{mes,2}}$$

where:
Z is a variable corresponding to the variable Y;
$Q_{mes,1}$ is the mass flow rate of the fuel gas in laminar flow through an apparatus giving rise to a measured pressure drop; and
$Q_{mes,2}$ is the mass flow rate of the fuel gas measured downstream from said apparatus giving rise to a pressure drop; and
A, B, and C are predetermined coefficients for the fuel gas family and correspond respectively to the coefficients $\alpha$, $\beta$, and $\gamma$.

It is possible to perform a calibration step with the reference gas, e.g. in order to obtain the values for the viscosity and the heat capacity of the reference gas.

This calibration step makes it possible to obtain measurements that are accurate, in particular for gases that are not pure, such as gases that contain dihydrogen.

The invention also provides a device for estimating at least one combustion characteristic of a fuel gas belonging to a family of fuel gases, said at least one characteristic being the Wobbe index or the higher heating value, the device comprising:
  at least two modules for measuring at least two flow properties of said fuel gas;
  a module for measuring the dihydrogen content $X_{H_2}$ contained in said fuel gas;
  a module configured to estimate said at least one characteristic $$\Xi_{\frac{GN}{H2}}$$

by means of the following empirical affine relationship:

$$\Xi_{\frac{GN}{H2}} = \alpha + \beta \cdot Y + \gamma \cdot X_{H_2}$$

where:
$\alpha$, $\beta$, and $\gamma$ are coefficients predetermined for the family of fuel gases; and
Y is a variable representative of physical properties of said fuel gas prepared from said measured values of said at least two flow properties of said fuel gas.

This device may be configured to perform all of the implementations of the method as described above.

It should be observed that this device may include a flow member in which the fuel gas flows so that its flow properties can be measured.

In a particular embodiment, said at least one combustion characteristic of the fuel gas comprises the Wobbe index $$IW_{\frac{GN}{H2}},$$

the device comprising:
  an inlet for receiving a stream of said fuel gas;
  an inlet for receiving a stream of a reference gas;
  a selector and guide module for bringing the stream of said fuel gas or the stream of said reference gas to a pipe;
  a fluid flow constriction; and
  a module for measuring a mass flow rate of the fuel gas in sonic flow through said fluid flow constriction, and including a submodule for measuring the absolute pressure upstream from the constriction and a submodule for measuring the absolute temperature upstream from the constriction;
  the empirical affine relationship used for estimating the Wobbe index $$IW_{\frac{GN}{H2}}$$

then being written:

$$IW_{\frac{GN}{H2}} = D + E \cdot Y + F \cdot X_{H_2}$$

with:

$$Y = \frac{Q_{mes,2}}{Q_{ref}} \cdot \frac{P_{ref}}{P_{mes}} \cdot \sqrt{\frac{T_{ref}}{T_{mes}}}$$

where:
$Q_{mes,2}$ is the measured mass flow rate of the fuel gas;
$P_{mes}$ is the measured absolute pressure of the fuel gas;
$T_{mes}$ is the measured absolute temperature of the fuel gas;
$Q_{ref}$ is the measured mass flow rate of the reference gas;
$P_{ref}$ is the measured absolute pressure of the reference gas; and
$T_{ref}$ is the measured absolute temperature of the reference gas; and
D, E, and F are predetermined coefficients for the fuel gas family and correspond respectively to the coefficients $\alpha$, $\beta$, and $\gamma$.

In a particular embodiment, the device is suitable for estimating the Wobbe index of said fuel gas, the device further comprising a module for measuring the density of said fuel gas and the module that is configured for estimating said at least one characteristic also being configured to estimate the higher heating value from the estimated Wobbe index and from the measured density of the gas.

In particular, the higher heating value can be obtained by multiplying the estimated Wobbe index by the square of the measured density.

By way of indication, it may be observed that it is possible to use a density sensor from the Swiss supplier TRAFAG and having the reference 8774.

In a particular embodiment, said at least one combustion characteristic of the fuel gas comprises the higher heating value $$HHV_{\frac{GN}{H2}},$$

the device comprising:
- an inlet for receiving a stream of said fuel gas;
- a module for measuring the mass flow rate of said fuel gas in laminar flow through an apparatus giving rise to a pressure drop, the measurement depending on the viscosity of the fuel gas and on the viscosity of a reference gas; and
- a module for measuring downstream from said apparatus giving rise to a pressure drop, the mass flow rate of said fuel gas by means of a thermal mass flow meter, the measurement depending on the specific heat capacity of the fuel gas and on the heat capacity of a reference gas;

the empirical affine relationship used for estimating the higher heating value $$HHV_{\frac{GN}{H2}}$$

then being written:

$$HHV_{\frac{GN}{H2}} = A + B \cdot Z + C \cdot X_{H_2}$$

with:

$$Z = \frac{Q_{mes,1}}{Q_{mes,2}}$$

where:
Z is a variable corresponding to the variable Y;
$Q_{mes,1}$ is the mass flow rate of the fuel gas in laminar flow through an apparatus giving rise to a measured pressure drop; and
$Q_{mes,2}$ is the mass flow rate of the fuel gas measured downstream from said apparatus giving rise to a pressure drop; and
A, B, and C are predetermined coefficients for the fuel gas family and correspond respectively to the coefficients α, β, and γ.

In a particular embodiment, the module configured for estimating said at least one characteristic $$\Xi_{\frac{GN}{H2}}$$

by means of the empirical affine relationship is also configured to estimate a stoichiometric volume of air or a combustibility index.

In a particular embodiment, the device further comprises a module for regulating said combustion characteristic of the fuel gas or for regulating the combustion characteristic of a fuel gas and an estimated stoichiometric volume of air or an estimated combustibility index corresponding to said estimated characteristic.

This regulation module may comprise in particular an actuator for injecting an additional gas, e.g. air. The regulation may be closed-loop regulation.

BRIEF DESCRIPTION OF THE DRAWINGS

Other characteristics and advantages of the present invention appear from the following description made with reference to the accompanying drawings, which show an example having no limiting character.

In the figures.

DETAILED DESCRIPTION

There follows a description of a method and a device for estimating a combustion characteristic of a fuel gas belonging to a family of fuel gases. The characteristic may be the Wobbe index or the higher heating value.

The invention is not limited in any way to estimating a single characteristic, and it may comprise estimating the Wobbe index and the higher heating value simultaneously.

Figure 1:
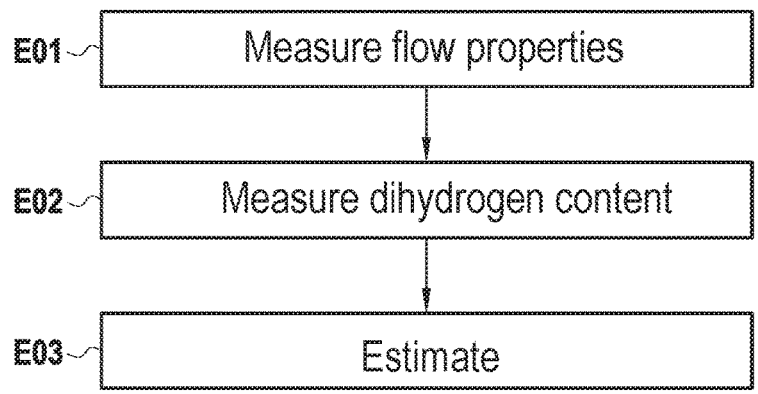
FIG. 1 is a diagram showing the steps of an example of a method of estimating a combustion characteristic.

FIG. 1 is a diagram showing the steps of a method of estimating a combustion characteristic of a fuel gas.

This method is particularly adapted to gases that might contain a non-zero quantity of dihydrogen, and in particular to fuel gases containing dihydrogen in the range 0% to 20%.

In a first step E01, at least two flow properties of the fuel gas are measured. The fuel gas under study is then flowing through a flow member and flow properties such as temperature, pressure, or indeed flow rate are measured, e.g. by means of sensors.

In a second step E02 the dihydrogen content in the flowing gas is measured, and written $X_{H_2}$. It may be observed that in all of the implementations and embodiments of the invention, the dihydrogen content may be a molar fraction or a volume fraction. If pressures are low enough, it may be assumed that the perfect gas law applies and that molar fractions and volume fractions have the same values. In applications of the invention, the dihydrogen content has the same value as a molar fraction or as a volume fraction. This step may be performed simultaneously with the step E01, or beforehand, or afterwards.

In a third step E03, the characteristic written $$\Xi_{\frac{GN}{H2}}$$

is estimated by means of the following empirical affine relationship:

$$\Xi_{\frac{GN}{H2}} = \alpha + \beta \cdot Y + \gamma \cdot X_{H_2}$$

where:

α, β, and γ are coefficients predetermined for the family of fuel gases; and

Y is a variable representative of physical properties of said fuel gas prepared from said measured values of said at least two flow properties of said fuel gas.

The measured values of said at least two flow properties of said fuel gas are selected specifically so that the variable Y can be both representative of the physical properties of the fuel gas, such as viscosity, specific heat capacity (per unit weight), or indeed density, and also capable of being expressed as a function of the measured values of the flow properties of the fuel gas.

Thus, by using the notation:

$U_{mes,1}$ for the measurement of the flow property $U_1$,
$U_{mes,2}$ for the measurement of the flow property $U_2$; and
$U_{mes,3}$ for the measurement of the flow property $U_3$, this gives:

$$Y = f(U_{mes,1}; U_{mes,2}; U_{mes,3})$$

Figure 2:
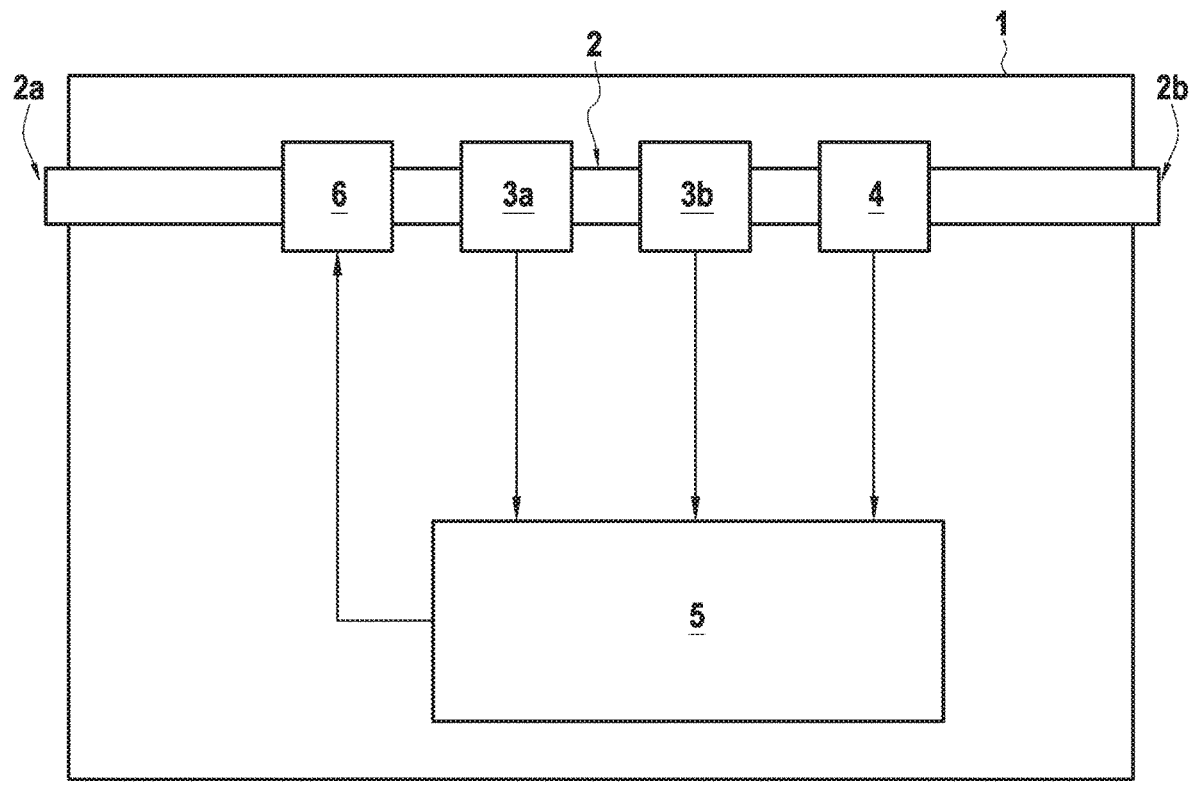
FIG. 2 is a diagram showing an example of a device for estimating a combustion characteristic.

FIG. 2 shows an embodiment of a device for estimating at least one combustion characteristic of a fuel gas belonging to a family of fuel gases.

The device is capable in particular of performing a method of the kind described with reference to FIG. 1.

In this example, the device 1 comprises a flow member 2 configured to receive a stream of fuel gas for which it is desired to estimate the Wobbe index or the higher heating value, for example. The flow member has an inlet 2a for receiving the stream of fuel gas, and an outlet 2b.

The device 1 also has two modules 3a and 3b for measuring flow properties of the fuel gas.

By way of example, the modules 3a and 3b may both, or each, measure a flow rate, a pressure, or indeed a temperature.

Specifically, the modules 3a and 3b are conventional sensors for measuring a flow rate, a pressure, or indeed a temperature.

The device 1 includes a module 4 for measuring a dihydrogen content $X_{H_2}$, e.g. a sensor that delivers a dihydrogen molar percentage.

The modules 3a, 3b, and 4 are in communication with an estimator module 5 so as to communicate the results of their respective measurements to the estimator module 5. The estimator module 5 may be a computer having a processor and a memory (not shown).

The module 5 is configured to estimate said at least one characteristic $$\Xi_{\frac{GN}{H2}}$$

by means of the following empirical affine relationship:

$$\Xi_{\frac{GN}{H2}} = \alpha + \beta \cdot Y + \gamma \cdot X_{H_2}$$

where:

α, β, and γ are coefficients predetermined for the family of fuel gases; and

Y is a variable representative of physical properties of said fuel gas prepared from said values of said at least two flow properties of said fuel gas, as measured by the modules 3a and 3b.

To this end, the module 5 may have, stored in memory, possible values for the predetermined coefficients α, β, and γ. The module 5 may also have computer program instructions stored in memory to enable it to execute the estimation.

By way of example, the computer program may comprise instructions for calculating the variable Y from the values measured by the modules 3a and 3b, and instructions for calculating the characteristic $$\Xi_{\frac{GN}{H2}}$$

by means of the above-defined function.

Optionally, the device 1 may include an actuator 6 controlled by the estimator module 5 in order to regulate at least said characteristic. By way of example, the actuator 6 may be a compressed air injector.

Figure 3:
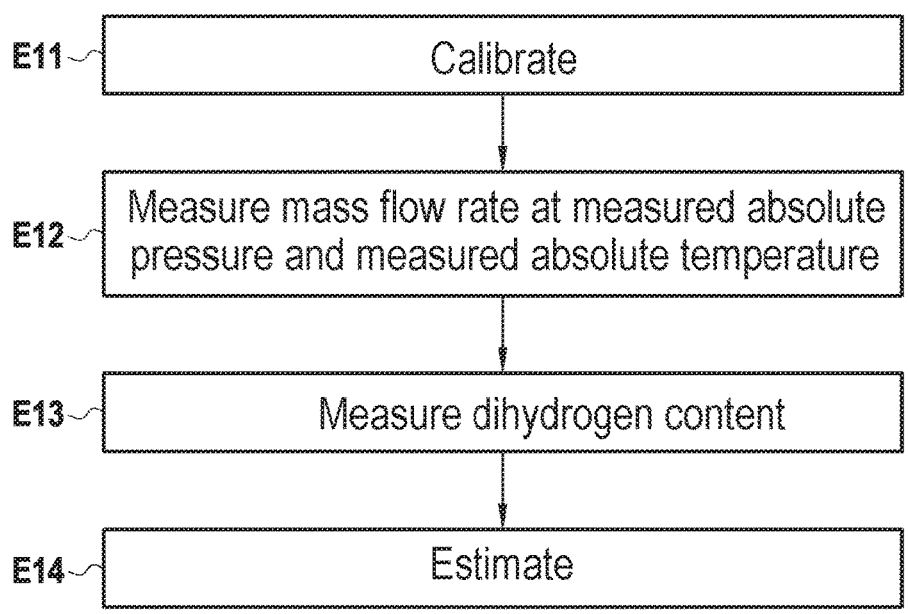
FIG. 3 is a diagram of the steps of a method of estimating the Wobbe index.
Figure 4:
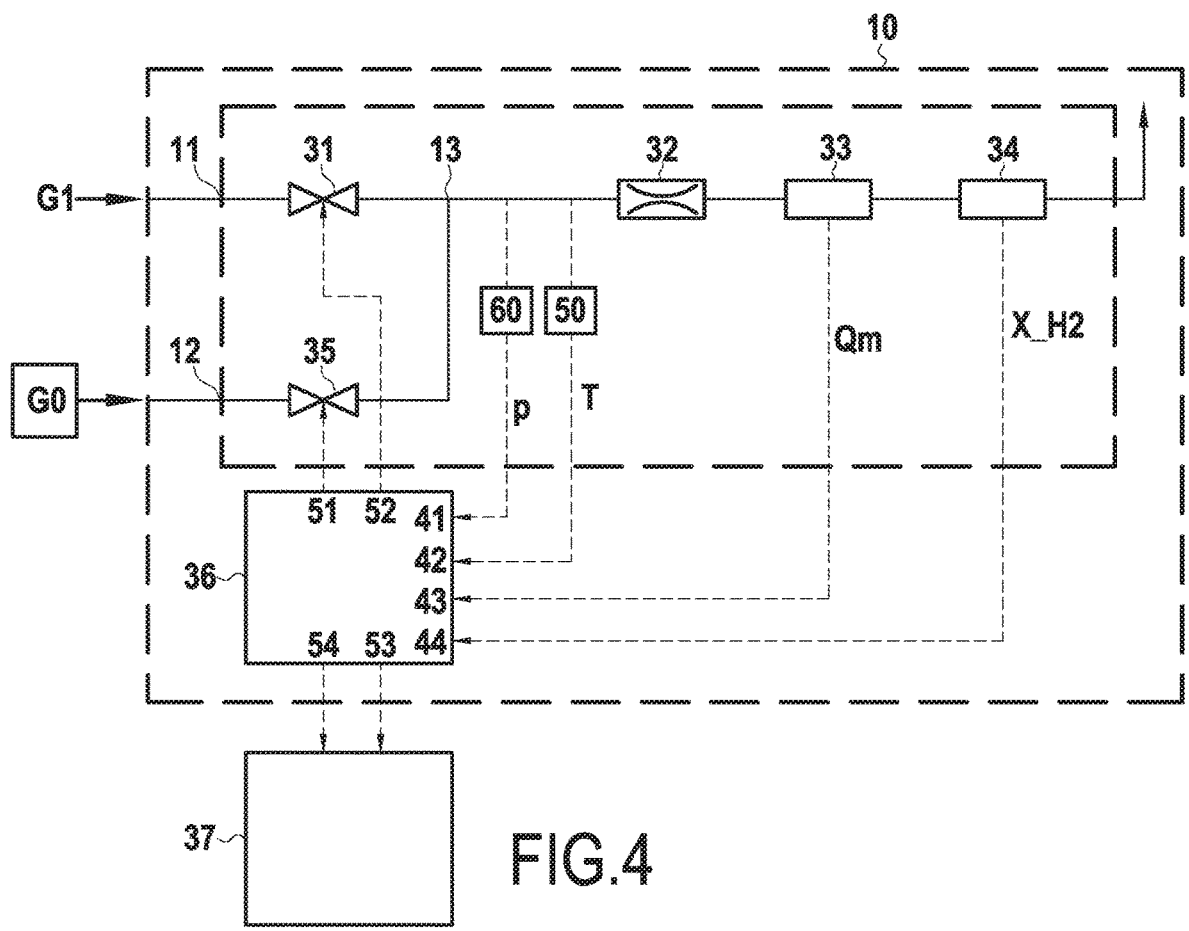
FIG. 4 is a diagram of an example of a device for estimating the Wobbe index.

With reference to FIGS. 3 and 4, there follows a description of an implementation and an embodiment in which the Wobbe index $$IW_{\frac{GN}{H2}}$$

of a fuel gas is estimated.

FIG. 3 shows the steps of a method of estimating the Wobbe index $$IW_{\frac{GN}{H2}}$$

of a fuel gas.

This method comprises a calibration first step E11, during which a measurement is taken of a mass flow rate of a reference gas (e.g. methane) in sonic flow through a fluid flow constriction (e.g. an orifice or a micro-nozzle), at a measured reference absolute pressure and at a measured reference absolute temperature.

In a second step E12, a measurement is taken of a mass flow rate of a fuel gas in sonic flow through the fluid flow constriction, this measurement being taken at an absolute pressure measured upstream from the constriction and at an absolute temperature measured upstream from the constriction.

In a step E13, the dihydrogen content $X_{H_2}$ is measured.

Steps E11 to E13 may be performed in any possible order. In particular, steps E12 and E13 may be performed simultaneously.

In a step E14, the Wobbe index $$IW_{\frac{GN}{H2}}$$

is estimated by an empirical affine relationship that is written:

$$IW_{\frac{GN}{H2}} = D + E \cdot Y + F \cdot X_{H_2}$$

with:

$$Y = \frac{Q_{mes,2}}{Q_{ref}} \cdot \frac{p_{ref}}{p_{mes}} \cdot \sqrt{\frac{T_{ref}}{T_{mes}}}$$

where:
$Q_{mes,2}$ is the measured mass flow rate of the fuel gas;
$p_{mes}$ is the measured absolute pressure of the fuel gas;
$T_{mes}$ is the measured absolute temperature of the fuel gas;
$Q_{ref}$ is the measured mass flow rate of the reference gas;
$p_{ref}$ is the measured absolute pressure of the reference gas; and
$T_{ref}$ is the measured absolute temperature of the reference gas; and
D, E, and F are predetermined coefficients for the fuel gas family and correspond respectively to the coefficients α, β, and γ.

In order to perform the steps E11 and E12, a fluid flow constriction is used, such as an orifice or a micro-nozzle of known shape.

On either side of the fluid flow constriction, the following measurements are taken: upstream from the fluid flow constriction, the absolute temperatures and the absolute pressures are measured; and downstream from the fluid flow constriction, the mass flow rate is measured (e.g. by means of a thermal mass flow meter).

Specifically, that corresponds to measuring the normal volume flow rate, written $Q_{vn}$, passing through the device, in two different ways.

Specifically, since the flow is sonic, the following applies:

$$Q_{vn} = k \cdot p \sqrt{\frac{T}{d}}$$

with:
k a constant characteristic of the shape of the orifice;
p and T the absolute pressure and the absolute temperature of the gas upstream from the orifice; and
d the density of the gas.

Also, by using a thermal mass flow meter, the following is obtained:

$$Q_{vn} = Q_{mes,2} \cdot C$$

with:
$Q_{vn,mes,2}$ the measurement taken by the thermal mass flow meter in step E12;
C a correction coefficient that takes account of the differences of the physical properties of the gas (e.g. its specific heat capacity, its viscosity, its thermal conductivity) compared with the properties of air.

For a gas of known composition, the following applies:

$$\frac{1}{C} = \Sigma \frac{X_i}{C_i}$$

with:
$X_i$ the volume fraction of the component i;
$C_i$ the correction coefficient relating to the component i. This coefficient can be read from a table associated with the thermal mass flow meter.

The calibration step E11 is a step during which the device is fed with a reference gas of composition that is accurately known (preferably pure methane).

The equality between the two flowrate relationships using the values obtained in the calibration procedure of step E11 can thus be written as follows:

$$Q_{vn,ref} \cdot C_{ref} = k \cdot p_{ref} \sqrt{\frac{T_{ref}}{d_{ref}}}$$

And, in the measuring procedure of step E12 in which measurements are taken on the fuel gas, the following applies:

$$Q_{mes,2} \cdot C = k \cdot p_{mes} \sqrt{\frac{T_{mes}}{d}}$$

By means of the measurement in step E14, the hydrogen content $X_{H_2}$ (e.g. in volume terms) is also known.

It may be observed that in the above equations, the only two parameters that are unknown are C and density d. It is then possible to eliminate the parameter k in order to express the variable Y, associated with C and with the density d.

Specifically, the following applies:

$$Y = \frac{C_{ref}}{C} \cdot \sqrt{\frac{d_{ref}}{d}}$$

And, Y is a variable representative of the physical properties of the fuel gas. It is possible to rewrite Y from the measured values. These measured values ($Q_{mes,2}$, p, and T) can be written $U_{mes,1}$ for the measured flow property $U_1$, $U_{mes,2}$ for the measured flow property $U_2$, and $U_{mes,3}$ for the measured flow property $U_3$, thus giving:

$$Y = f(U_{mes,1}; U_{mes,2}; U_{mes,3})$$

Where:
$U_{mes,1} = p_{mes}$;
$U_{mes,2} = Q_{mes,2}$; and
$U_{mes,3} = T_{mes}$ Finally, the following applies:

$$Y = \frac{C_{ref}}{C} \cdot \sqrt{\frac{d_{ref}}{d}} = \frac{Q_{mes,2}}{Q_{ref}} \cdot \frac{p_{ref}}{p_{mes}} \cdot \sqrt{\frac{T_{ref}}{T_{mes}}}$$

This definition of the variable Y can be used in an empirical affine relationship having as its variable Y, and that is written in the following form:

$$IW_{\frac{GN}{H2}} = D + E \cdot Y + F \cdot X_{H_2}$$

D, E, and F being predetermined coefficients for the fuel gas family and corresponding respectively to the coefficients α, β, and γ described with reference to FIGS. 1 and 2.

The coefficients D, E, and F can be obtained from known gas compositions, e.g. compositions of natural gas in the network of a country or a region. By way of example, it is possible to use known compositions for higher heating value gas distributed in Europe and well known to the person skilled in the art.

From these known compositions, it is possible to define limit values concerning the molar fractions of the various compounds. For example, by using the notation $X_K$ for the molar fraction of the species K in a gas, it is possible to have known compositions of the following type:

$$0\% < X_{N2} < 5.5\%$$

$$0.5\% < X_{C2H6} < 12.5\%$$

$$0\% < X_{C4H10} < 3.5\%$$

$$0\% < X_{CO2} < 1.3\%$$

$$0\% < X_{C3H8} < 3.5\%$$

$$0\% < X_{C5H12} < 3.5\%$$

$$X_{CH4} = 1 - \Sigma X_K$$

It should be observed that there is no dihydrogen in present-day gas compositions.

These possible ranges enable gas compositions to be generated randomly for which it is possible to determine the Wobbe index (or even the higher heating value). 10,000 gases can thus be generated.

For each randomly generated gas, it is possible to add a random dihydrogen quantity lying in the range 0% to 20% molar fraction. Once more, it is possible to determine the Wobbe index for these randomly generated gases.

It is also possible to deduce from the randomly generated compositions the associated values for the variable Y. By applying a least squares method, it is possible to obtain values for the coefficients D, and F:

$$IW_{\frac{GN}{H2}} = -18.0272 + 32.85887 \cdot Y - 0.11633 \cdot X_{H_2}$$

These results were obtained by using methane as the reference gas.

It may be observed that for a dihydrogen molar fraction lying in the range 0% to 20%, the error in estimating the Wobbe index is always less than 1.4%, and that it is less than 1% in 98% of the 10,000 gases that were obtained randomly.

Alternatively, it is possible to use a correlation in which the coefficients are not constants but depend on the dihydrogen content as a molar fraction.

The empirical affine relationship may be rewritten as follows:

$$IW_{\frac{GN}{H2}} = D(X_{H_2}) + E(X_{H_2}) \cdot Y$$

In this example, D and E are functions of the dihydrogen content (the equation has been rewritten so as to show only two coefficients that depend on $X_{H_2}$, nevertheless, it is possible to write the equation with three coefficients).

In the same manner, by generating random gas compositions, the inventors have observed that it is possible to use functions D and that are piecewise constant over dihydrogen concentration ranges of width 1%.

For example, in the range 2% to 3% dihydrogen, D and E take the following values:
D=−18.181
E=32.75

It has been observed that the error in estimating the Wobbe index is then always less than 1% for 95% of the 10,000 random gases.

FIG. 4 shows a device for estimating the Wobbe index and that is capable of implementing the method as described with reference to FIG. 3.

This device 10 has an inlet 11 for receiving a fuel gas G1 and an inlet 12 for receiving a reference gas G2 (typically methane).

The device 10 also has a selector and guide module for bringing the fuel gas stream or the reference gas stream to the inlet of a pipe 13. Specifically, the selector and guide module comprises a valve 31 and a valve 35.

The valves 31 and 35 are controlled by a module 36 via respective terminals 52 and 51 so as to cause either the fuel gas or else the reference gas to flow into the pipe.

In this example, the pipe comprises, from upstream to downstream starting from its inlet 13:

An absolute pressure sensor 60 connected to the module 36 via its terminal 41;
An absolute temperature sensor 50 connected to the module 36 via its terminal 42;
A fluid flow constriction 32 (e.g. an orifice or a micro-nozzle);
A thermal mass flow rate sensor 33 connected to the module 36 via its terminal 43; and
A sensor 34 for sensing the dihydrogen molar fraction and connected to the module 36 via its terminal 44.

The module 36 can apply an empirical affine relationship such as those described above in order to estimate the Wobbe index from the signals received at the terminals 41 to 44.

In the example shown, the module 36 communicates via two output terminals 54 and 53 with an external module 37, e.g. an actuator for performing regulation, or indeed a display. In a variant that is not shown, the module 37 is integrated in the device 10.

Figure 5:
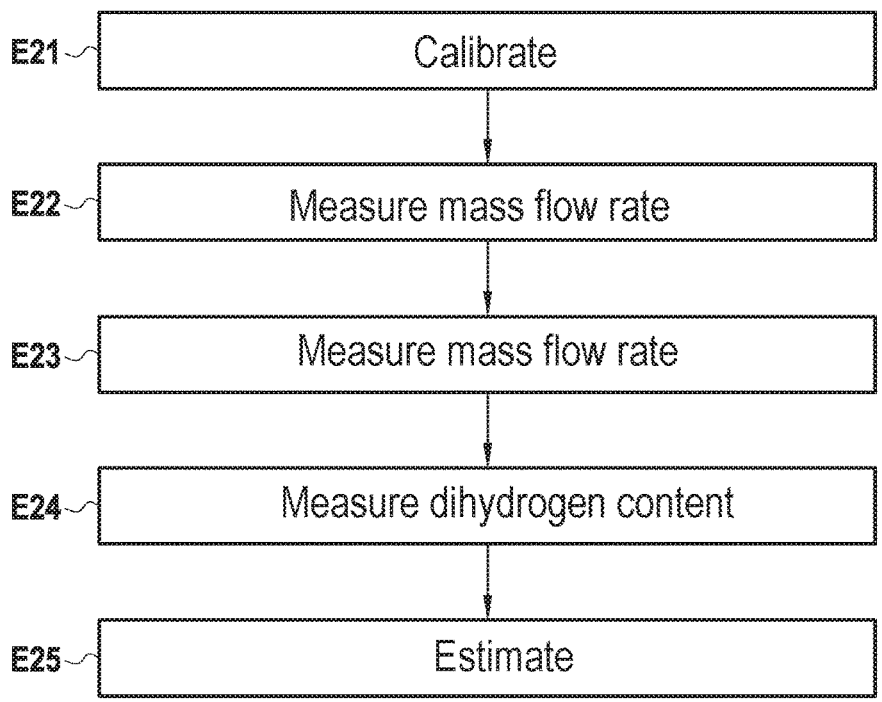
FIG. 5 is a diagram of the steps of a method of estimating the higher heating value.
Figure 6:
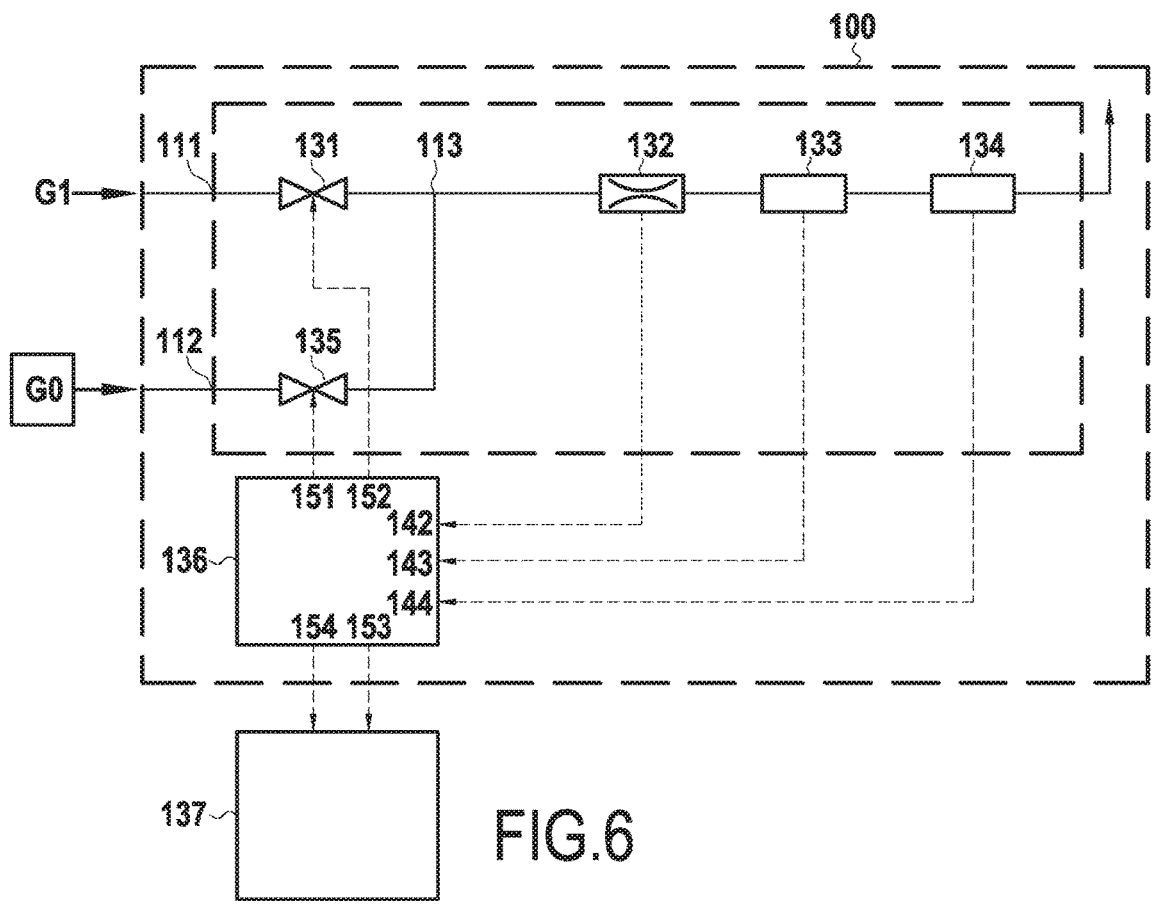
FIG. 6 is a diagram showing an example of a device for estimating the higher heating value.

With reference to FIGS. 5 and 6, there follows a description of an implementation and an embodiment in which the higher heating value of a fuel gas is estimated.

FIG. 5 shows the steps of a method of estimating the higher heating value $$HHV_{\frac{GN}{H2}};$$

of a fuel gas.

In a step E22, the mass flow rate of said fuel gas is measured in laminar flow through an apparatus giving rise to a pressure drop, this measurement depending on the viscosity of the fuel gas and on the viscosity of a reference gas.

In a step E23, downstream from said apparatus giving rise to a pressure drop, the mass flow rate of said fuel gas is measured by means of a thermal mass flow meter, the measurement depending on the specific heat capacity of the fuel gas and on the heat capacity of the reference gas.

In a step E21, which may be performed before or after performing the steps E22 and E23, a calibration step is performed that corresponds to performing the steps E22 and E23, but with a reference gas (e.g. methane).

A step E24 is also performed of measuring the dihydrogen content $X_{H_2}$, as a molar fraction.

Finally, in a step E25, the higher heating value is estimated by means of an empirical affine relationship having the form:

$$HHV_{\frac{GN}{H2}} = A + B \cdot Z + C \cdot X_{H_2}$$

with:

$$Z = \frac{Q_{mes,1}}{Q_{mes,2}}$$

where:

Z is a variable corresponding to the variable Y described with reference to FIG. 1;

$Q_{mes,1}$ is the mass flow rate of the fuel gas in laminar flow through an apparatus giving rise to a measured pressure drop; and $Q_{mes,2}$ is the mass flow rate of the fuel gas measured downstream from said apparatus giving rise to a pressure drop; and A, B, and C are predetermined coefficients for the fuel gas family and correspond respectively to the coefficients α, β, and γ.

The following relationship for higher heating value (HHV) is known from prior document DE 4 118 781:

$$HHV = \alpha \cdot \left(\frac{\rho C_p}{\mu}\right) + \beta$$

with:

α and β predetermined constants;
ρ the density of the fuel gas;
μ the viscosity of the fuel gas; and
$C_P$ the heat capacity of the fuel gas.

The following dimensionless variable Z can be defined as follows:

$$Z = \frac{(\rho C_p / \mu)_{GN}}{(\rho C_p / \mu)_{ref}}$$

Here, the subscript GN specifies the fuel gas, and ref specifies a reference gas.

The relationship concerning the higher heating value can be rewritten as follows:

$$HHV_{GN} = A \cdot Z + B$$

In order to measure Z, the two flow rate measurements are used. By way of example, $Q_{mes,1}$ is the mass flow rate of the fuel gas in laminar flow through an apparatus giving rise to a measured pressure drop. By using Poiseuille's law, it is known that the apparatus subjects the gas stream to a pressure drop through a laminar element.

Since the measurement depends on viscosity, for certain measuring apparatuses, it has a form that depends on the upstream-to-downstream pressure difference $\Delta p_{mes}$ and the flowmeter that delivers $Q_{mes,1}$ can determine the volume flow rate by means of the following formula:

$$Q_{vol,1} = K_1 \cdot \frac{\Delta p_{mes}}{\mu}$$

Where $K_1$ is a geometrical constant.

In this example, a pressure sensor and a temperature probe are integrated in the flowmeter and they make it possible to obtain directly the mass flow rate $Q_{mes,1}$ (or volume flow rate reduced to normal temperature and pressure conditions), as follows:

$$Q_{mez,1}[Nm^3/h] = Q_{vol,1}[m^3/h] \cdot \frac{p_{mes}}{p_0} \cdot \frac{T_0}{T_{mes}}$$

The measurement of the corrected volume flow rate $Q_{mes,1}$ depends on the viscosity of the fuel gas.

The flow rate $Q_{mes,2}$ is measured using a thermal mass flow meter. The measurement of the mass flow rate $Q_{mes,2}$ depends on the specific heat capacity of the fuel gas.

In this way, two estimates are obtained of the mass flow rate, each presenting a respective error relative to the real normal volume flow rate ($Q_{vn}$). The following applies:

$$Q_{mes,1} - Q_{vn} \frac{\mu_{GN}}{\mu_{ref}}$$

$$Q_{mes,2} - Q_{vn} \frac{(\rho C_p)_{GN}}{(\rho C_p)_{ref}}$$

For $Q_{mes,1}$, the error is associated with the difference between the real viscosity of the mixture gas and the viscosity of the reference gas (methane in this example).

For $Q_{mes,2}$, the error is associated with the difference between the density multiplied by the real specific heat capacity of the mixture gas, and by the same quantity for the reference gas (methane in this example).

By taking the ratio of the two measured flow rates, the variable Z is determined and the correlation relationship of Document DE 4 118 781 becomes:

$$HHV_{GN} = A \cdot \frac{Q_{vn} \frac{\mu_{gn}}{\mu_{ref}}}{Q \frac{(\rho C_p)_{GN}}{(\rho C_p)_{ref}}} + B$$

By writing:
$U_{mes,1} = Q_{mes,1}$; and
$U_{mes,2} = Q_{mes,2}$
The following applies:

$$Z = f(U_{mes,1}; U_{mes,2}) = \frac{Q_{mes,1}}{Q_{mes,2}}$$

Nevertheless, the inventors have observed that this relationship is not applicable once dihydrogen is present in the fuel gas. Specifically, the measurement error becomes too large, dihydrogen has properties (viscosity, specific heat capacity) that are very different from those of gases such as alkanes.

In order to mitigate that drawback, use is made of the measured dihydrogen content $X_{H_2}$, and the following equation is proposed:

$$PCS_{\frac{GN}{H2}} = A + B \cdot Z + C \cdot X_{H_2}$$

A, B, and C being predetermined coefficients for the fuel gas family and corresponding respectively to the coefficients α, β, and γ described with reference to FIGS. 1 and 2.

The coefficients A, B, and C can be obtained from known gas compositions, e.g. compositions of natural gas in the network of a country or a region. By way of example, it is possible to use known compositions for high heating value gas distributed in Europe and well known to the person skilled in the art.

From these known compositions, it is possible to define limit values concerning the molar fractions of the various compounds. For example, by using the notation XK for the molar fraction of the species K in a gas, it is possible to have known compositions of the following type:

$0\% < X_{N2} < 5.5\%$ $0.5\% < X_{C2H6} < 12.5\%$ $0\% < X_{C4H10} < 3.5\%$ $0\% < X_{CO2} < 1.3\%$ $0\% < X_{C3H8} < 3.5\%$ $0\% < X_{C5H12} < 3.5\%$ $X_{CH4} = 1 - \Sigma X_K$ It should be observed that there is no dihydrogen in present-day gas compositions.

These possible ranges make it possible to generate random gas compositions for which it is possible to determine the higher heating value. 10,000 gases can thus be generated.

For each randomly generated gas, it is possible to add a random dihydrogen quantity lying in the range 0% to 20% molar fraction. Here likewise, it is possible to determine the higher heating value of these randomly-generated gases.

It is also possible to deduce from the randomly-generated compositions the associated values for the variable Z. By applying a least squares method, it is possible to obtain values for the coefficients A, B, and C:

A=0.61650996

B=10.428

C=−0.0645996

Alternatively, it is possible to use a correlation in which the coefficients are not constants but depend on the dihydrogen content as a molar fraction.

The empirical affine relationship may be rewritten as follows:

$$HHV_{\frac{GN}{H2}} = A(X_{H_2}) + B(X_{H_2}) \cdot Z$$

In this example, A and B are functions of the dihydrogen content (the equation has been rewritten so as to show only two coefficients that depend on $X_{H_2}$ nevertheless, it is possible to write the equation with three coefficients).

In the same manner, by generating random gas compositions, the inventors have observed that it is possible to use functions A and B that are piecewise constant over dihydrogen concentration ranges of width 1%.

For example, in the range 19% to 20% dihydrogen, A and B take the following values:

A=0.397217

B=10.189715

FIG. 6 shows a device for estimating the higher heating value that is suitable for performing the method as described with reference to FIG. 5.

This device 100 has an inlet 111 for receiving a fuel gas G1 and an inlet 112 for receiving a reference gas G2 (typically methane).

The device 100 also has a selector and guide module for bringing the fuel gas stream or the reference gas stream to the inlet of a pipe 113. Specifically, the selector and guide module comprises a valve 131 and a valve 135.

The valves 131 and 135 are controlled by a module 136 via respective terminals 152 and 151 so as to cause either the fuel gas or else the reference gas to flow into the pipe.

In this example, the pipe comprises, from upstream to downstream and starting from its inlet 113:

A sensor 132 for sensing mass flow rate in laminar flow through an apparatus that gives rise to a pressure drop, the measurement depending on the viscosity of the fuel gas and on the viscosity of the reference gas, the sensor being connected to the module 136 via its terminal 142;

A sensor 133 for sensing thermal mass flow rate, the measurement depending on the specific heat capacity of the measured gas and on the specific heat capacity of the reference gas, the sensor being connected to the module 136 via its terminal 143; and A sensor 134 for sensing the dihydrogen molar fraction and connected to the module 136 via its terminal 144.

The module 136 can apply an empirical affine relationship such as those described above in order to estimate the higher heating value from the signals received at the terminals 142 to 144.

In the example shown, the module 136 communicates via two output terminals 154 and 153 with an external module 137, e.g. an actuator for performing regulation, or indeed a display. In a variant that is not shown, the module 137 is integrated in the device 100.

Figure 7:
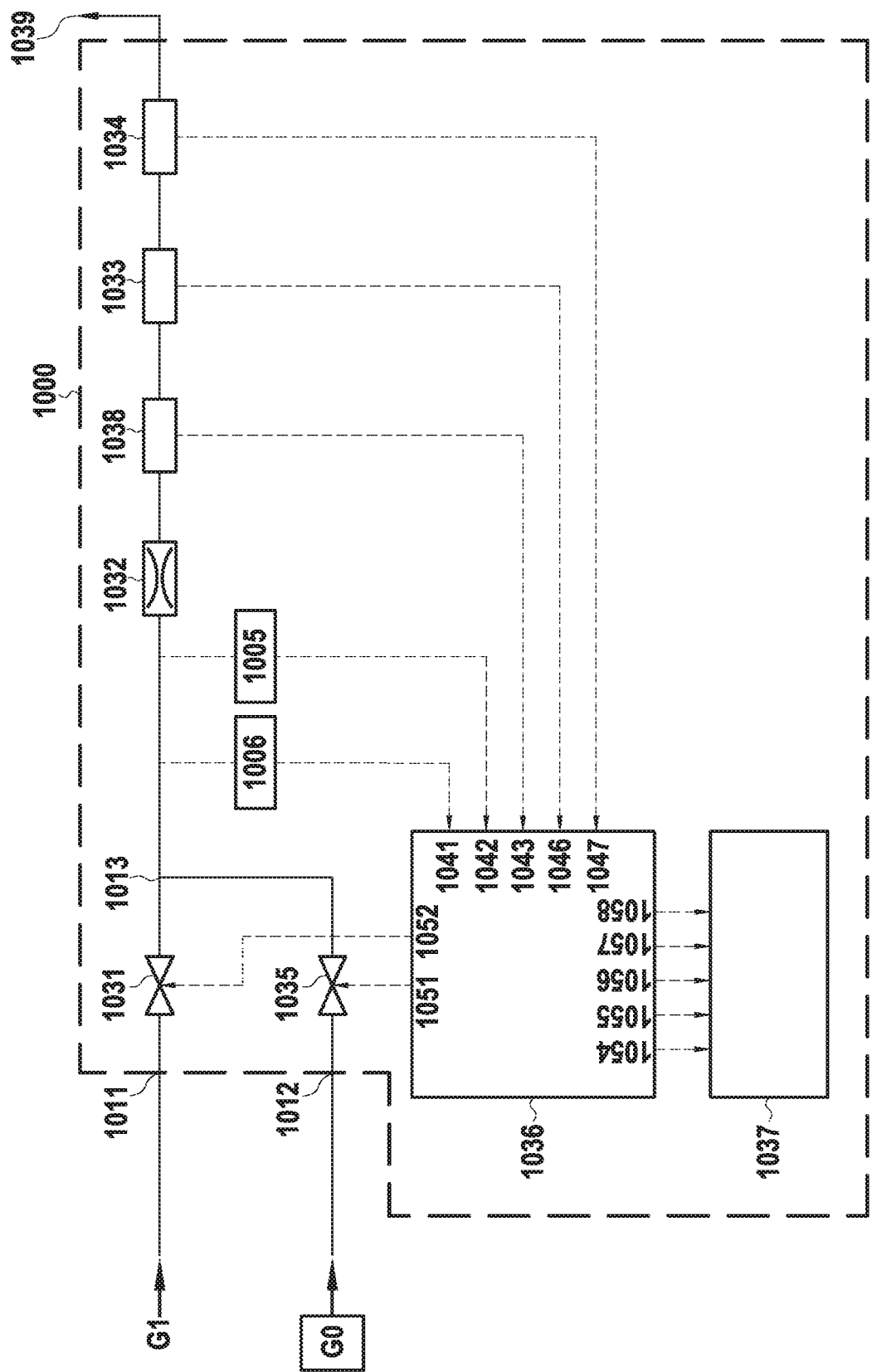
FIG. 7 is a diagram showing an example of a device for estimating the Wobbe index and the higher heating value.

FIG. 7 shows an example of a device capable of determining simultaneously the higher heating value and the Wobbe index by means of two empirical affine relationships.

This device has two inlets for gas under pressure. A first inlet 1011 is for receiving a fuel gas G1 belonging to a family of gases (e.g. the fuel gas in the second family specified in French standard NF EN 437) and also containing dihydrogen. The device 1000 has another inlet 1012 for a reference gas G0 used for the calibration stages.

The device 1000 also has a selector and guide module for bringing the stream of the fuel gas G1 or of the reference gas G0 to the inlet of a pipe 1013. The selector and guide module comprises a valve 1031 and a valve 1035.

The valves 1031 and 1035 are controlled by a module 1036 via respective terminals 1052 and 1051 so as to cause either the fuel gas or else the reference gas to flow into the pipe.

Starting from the inlet of the pipe 1013, and going from upstream to downstream, there are to be found:

An absolute pressure sensor 1006 connected to the module 1036 via its terminal 1041. This sensor delivers the value $P_{mes}$ measured on the fuel gas and the value $P_{ref}$ measured on the reference gas.

An absolute temperature sensor 1005 connected to the module 1036 via its terminal 1042. This sensor delivers the value $T_{mes}$ measured on the fuel gas and the value $T_{ref}$ measured on the reference gas.

A fluid flow constriction 1032 (e.g. an orifice or a micro-nozzle);

A sensor for sensing of the mass flow rate through a laminar pressure drop connected to the module 1036 via its terminal 1043. This sensor delivers the value $Q_{mes,1}$.

A thermal mass flow rate sensor 1033 connected to the module 1036 via its terminal 1046. This sensor delivers the value $Q_{mes,2}$ measured on the fuel gas and the value $Q_{ref}$ measured on the reference gas.

A sensor 1034 for sensing the dihydrogen molar fraction and connected to the module 36 via its terminal 1047.

A vent (39).

In this example, the module 1036 can calculate the following two variables:

$$Y = \left(\frac{p_{ref}}{p_{mes}} \cdot \sqrt{\frac{T_{ref}}{T_{mes}}}\right) \cdot \left(\frac{Q_{mes,2}}{Q_{ref}}\right)$$

$$Z = \frac{Q_{mes,2}}{Q_{mes,1}}$$

The module 1036 can then use the following formulae for determining the Wobbe index $$IW_{\frac{GN}{H2}},$$

the higher heating value $$HHV_{\frac{GN}{H2}},$$

the stoichiometric volume of air $$V_{a\frac{GN}{H2}},$$

combustibility index $$B_{\frac{GN}{H2}}$$

and the density of the fuel gas mixture $$d_{\frac{GN}{H2}}: IW_{\frac{GN}{H2}} = D + E \cdot Y + F \cdot X_{H_2}$$

$$HHV_{\frac{GN}{H2}} = A + B \cdot Z + C \cdot X_{H_2}$$

$$d_{\frac{GN}{H2}} = \left(\frac{HHV_{\frac{GN}{H2}}}{IW_{\frac{GN}{H2}}}\right)^2$$

$$V_{a\frac{GN}{H2}} = \frac{HHV_{\frac{GN}{H2}}}{0.000953 \cdot X_{H_2} + 1.165475}$$

$$B_{\frac{GN}{H2}} = \frac{IW_{\frac{GN}{H2}}}{0.000953 \cdot X_{H_2} + 1.165475}$$

Specifically, it is possible to determine the stoichiometric volume of air Va, the combustibility index B, and the density of the fuel gas mixture from the values for the Wobbe index IW and for the higher heating value HHV.

More precisely, for the natural gases usually distributed in Europe (and presently not containing any dihydrogen, the following applies:

$$\frac{HHV}{Va} = \frac{IW}{B} = 1.162$$

The inventors have observed that in the presence of dihydrogen, the values may depart from 1.162.

It is possible to associate the ratio of the higher heating value to the stoichiometric volume of air to the (known) dihydrogen content, and to do so with an error of less than 0.3% for all the natural gases that have been studied.

In other words, knowing the dihydrogen content and the estimated higher heating value with an error of less than 1% makes it possible to know the stoichiometric volume of air and thus to be able to regulate combustion with open-loop regulation.

In the same manner, the ratio of the Wobbe index to the combustibility index varies linearly with the dihydrogen content. This also makes it possible to perform open-loop regulation.

It may be observed that the error in estimating the combustibility index is less than 1% in 99.5% of the 10,000 gases of random composition, if 10,000 gases are used.

By definition of the Wobbe index, it is possible to determine the density of the gas, providing both the Wobbe index and the higher heating value are known.

It may be observed that the device 1000 delivers a Wobbe index signal at its terminal 1054, a higher heating value signal at its terminal 1055, a density signal at its terminal 1056, a stoichiometric volume of air signal at its terminal 1057, and a combustibility index signal at its terminal 1058. These signals relate to the fuel gas under study, i.e. to the gas G1.

Figure 8:
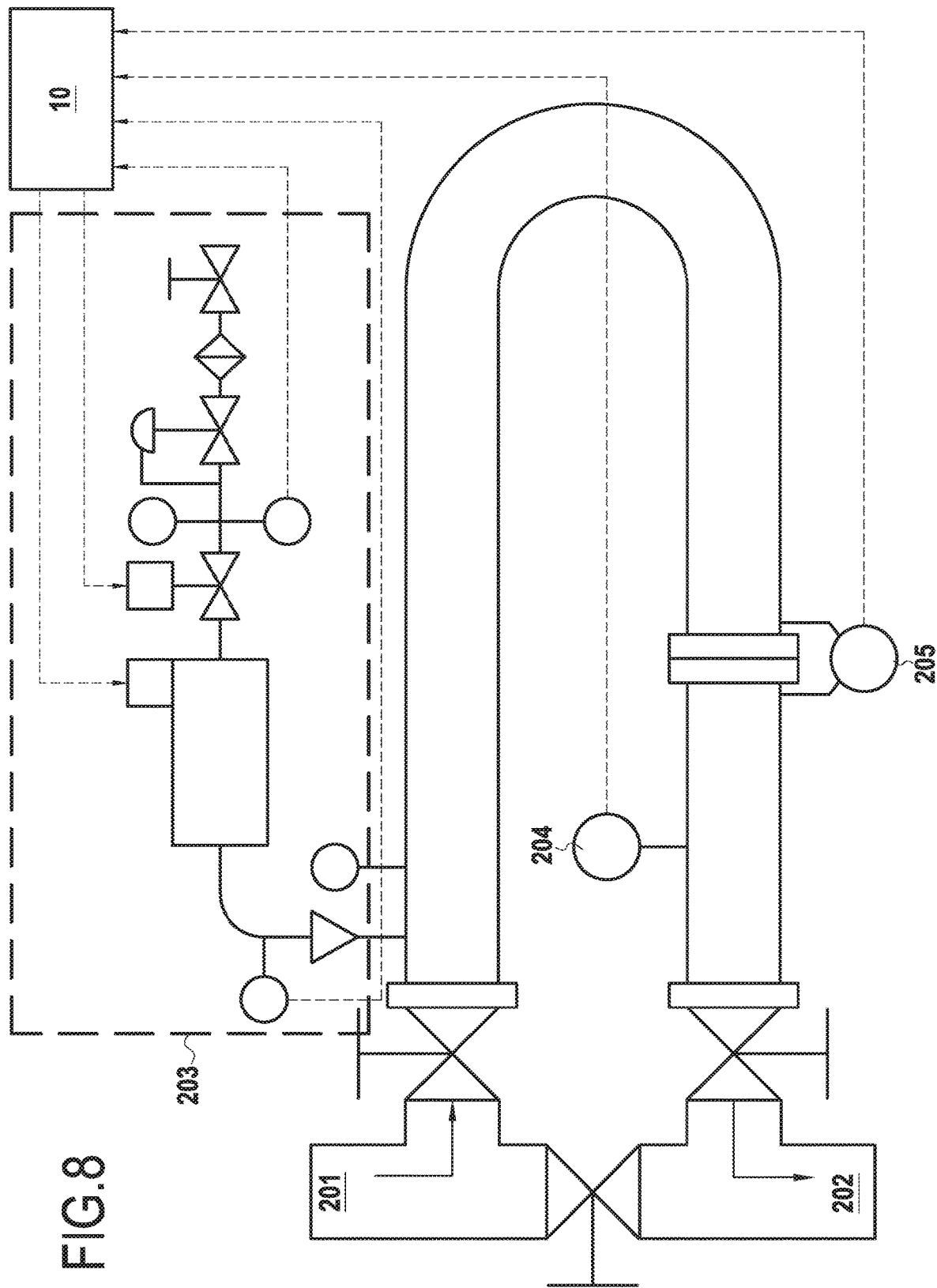
FIG. 8 is a diagram of an example of a device for regulating the Wobbe index.

FIG. 8 shows an example regulation application making use of the device 10 described with reference to FIG. 4. This device is connected between two points of a pipe, an inlet point 201 and an outlet point 202. The device 10 controls a compressed air supply module 203 as a function of the measurements taken by the sensors 205.

This apparatus is capable in particular of continuously regulating the Wobbe index for gases analogous to those distributed in Europe, plus an additional quantity of dihydrogen. In particular, it is because the measurement is continuous or in real time that it becomes possible to perform regulation, whereas that is not possible with apparatuses of the chromatograph type.

The accuracy with which the Wobbe index is measured is of the order of 1%.

It may be observed that it is possible to modify a setpoint value for the Wobbe index in the device 10 in order to obtain the desired regulation.

Furthermore, the calibration steps can be performed automatically while using methane. Starting stages can also be performed automatically, i.e. without operator intervention.

In addition, combined regulation is possible in which closed-loop regulation is performed on one of the characteristics (e.g. the Wobbe index) and open-loop regulation is performed on a flow rate of compressed air to be injected. This makes it possible to take account in particularly accurate manner of variations in the characteristic in order to satisfy more closely a setpoint for the characteristic.

It may be observed that such apparatus may consume natural gas at a rate of less than 150 liters per hour (L/h).

The implementations and embodiments described above enable thermodynamic data (Cp, viscosity) to be coupled with a measurement of dihydrogen content in volume or in molar fraction. Using an appropriate correlation makes it possible to calculate the Wobbe index and/or the higher heating value.

It may be observed that compared with using a gas phase chromatograph, the following applies:
- estimation is almost instantaneous (with a response time that may be less than 5 seconds (s));
- estimation is inexpensive.

Compared with existing correlation methods, good accuracy is obtained even though dihydrogen is present, together with good measurement robustness.

Finally, compared with apparatuses making use of combustion (combustibility meter or calorimeter), the invention provides good robustness, ease of implementation, and maintenance that is reduced and easy to perform.

The invention claimed is:

1. A method of estimating at least one combustion characteristic of a fuel gas belonging to a family of fuel gases, the at least one combustion characteristic comprising at least one of a Wobbe index or a higher heating value, the method comprising:
   measuring at least two flow properties of the fuel gas, the at least two flow properties comprising two or more of: a flow rate, a temperature, or a pressure;
   measuring a dihydrogen content $X_{H_2}$ contained in the fuel gas; and
   estimating, using at least one processor, the at least one combustion characteristic $$\Xi_{\frac{GN}{H2}}$$

using an empirical affine relationship of:

$$\Xi_{\frac{GN}{H2}} = \alpha + \beta \cdot Y + \gamma \cdot X_{H_2}$$

where:
   $\alpha$, $\beta$, and $\gamma$ are coefficients predetermined for the family of fuel gases; and
   Y is a variable representative of physical properties of the fuel gas prepared from the measurements of the at least two flow properties of the fuel gas, the physical properties of the fuel gas comprising at least one of: a viscosity, a specific heat capacity, or a density of the fuel gas.

2. The method according to claim 1, wherein the coefficients $\alpha$, $\beta$, and $\gamma$ are coefficients read from a chart having as input the measurement of the dihydrogen content $X_{H_2}$ and delivering as output the coefficients $\alpha$, $\beta$, and $\gamma$.

3. The method according to claim 2, wherein the chart associates different values of the coefficients $\alpha$, $\beta$, and $\gamma$ with different value ranges for the dihydrogen content $X_{H_2}$, the different value ranges each having a width of 1%.

4. The method according to claim 1, wherein values of the coefficients $\alpha$, $\beta$, and $\gamma$ are obtained from a dataset relating to known gases of the family of fuel gases for which values of Y and combustion characteristics that are representative of the physical properties are known.

5. The method according to claim 4, further comprising:
   randomly generating combustion characteristics and values for Y that are representative of the physical properties from the dataset relating to the known gases of the family of fuel gases.

6. The method according to claim 1, wherein the Wobbe index and the higher heating value are estimated using two empirical affine relationships.

7. The method according to claim 6, further comprising:
   estimating the density of the fuel gas from the estimated Wobbe index and from the estimated higher heating value.

8. The method according to claim 1, further comprising:
   regulating the at least one combustion characteristic of the fuel gas or regulating the at least one combustion characteristic of the fuel gas and an estimated stoichiometric volume of air or an estimated combustibility index corresponding to the at least one combustion characteristic.

9. The method according to claim 1, wherein:
   the at least one combustion characteristic of the fuel gas comprises the Wobbe index $$IW_{\frac{GN}{H2}};$$

measuring the at least two flow properties of the fuel gas includes measuring a mass flow rate of the fuel gas in sonic flow through a fluid flow constriction, the measurement being taken at an absolute pressure measured upstream from the constriction and at an absolute temperature measured upstream from the constriction;
   the method further comprises performing a calibration procedure during which a measurement is taken of a mass flow rate of a reference gas in sonic flow through the fluid flow constriction at a measured reference absolute pressure and at a measured reference absolute temperature; and
   an empirical affine relationship used for estimating the Wobbe index $$IW_{\frac{GN}{H2}}$$

is expressed as:

$$IW_{\frac{GN}{H2}} = D + E \cdot Y + F \cdot X_{H_2}$$

with:

$$Y = \frac{Q_{mes,2}}{Q_{ref}} \cdot \frac{P_{ref}}{P_{mes}} \cdot \sqrt{\frac{T_{ref}}{T_{mes}}}$$

where:
- $Q_{mes,2}$ is the measured mass flow rate of the fuel gas;
- $p_{mes}$ is the measured absolute pressure of the fuel gas;
- $T_{mes}$ is the measured absolute temperature of the fuel gas;
- $Q_{ref}$ is the measured mass flow rate of the reference gas;
- $p_{ref}$ is the measured absolute pressure of the reference gas;
- $T_{ref}$ is the measured absolute temperature of the reference gas; and
- D, E, and F are predetermined coefficients for the family of fuel gases and correspond respectively to the coefficients $\alpha$, $\beta$, and $\gamma$.

10. The method according to claim 1, wherein:
the Wobbe index of the fuel gas is estimated; and
the method further comprises measuring the density of the fuel gas and estimating the higher heating value from the estimated Wobbe index and from the density of the fuel gas.

11. The method according to claim 1, wherein:
the at least one combustion characteristic of the fuel gas comprises the higher heating value $$HHV_{\frac{GN}{H2}}$$

measuring the at least two flow properties of the fuel gas comprises:
- measuring a mass flow rate of the fuel gas in laminar flow through an apparatus giving rise to a pressure drop, the measurement depending on the viscosity of the fuel gas and on a viscosity of a reference gas; and
- measuring, downstream from the apparatus giving rise to the pressure drop, the mass flow rate of the fuel gas using a thermal mass flow meter, the measurement depending on the specific heat capacity of the fuel gas and on a heat capacity of the reference gas; and an empirical affine relationship used for estimating the higher heating value $$HHV_{\frac{GN}{H2}}$$

is expressed as:

$$HHV_{\frac{GN}{H2}} = A + B \cdot Z + C \cdot X_{H_2}$$

with:

$$Z = \frac{Q_{mes,1}}{Q_{mes,2}}$$

where:
- Z is a variable corresponding to the variable Y;
- $Q_{mes,1}$ is the mass flow rate of the fuel gas in laminar flow through the apparatus giving rise to the pressure drop;
- $Q_{mes,2}$ is the mass flow rate of the fuel gas measured downstream from the apparatus giving rise to the pressure drop; and
- A, B, and C are predetermined coefficients for the family of fuel gases and correspond respectively to the coefficients $\alpha$, $\beta$, and $\gamma$.

12. A device for estimating at least one combustion characteristic of a fuel gas belonging to a family of fuel gases, the at least one combustion characteristic comprising at least one of a Wobbe index or a higher heating value, the device comprising:
- at least two first sensors configured to measure at least two flow properties of the fuel gas, the at least two flow properties comprising two or more of: a flow rate, a temperature, or a pressure;
- a second sensor configured to measure a dihydrogen content $X_{H_2}$ contained in the fuel gas; and
- a processor configured to estimate the at least one characteristic $$\Xi_{\frac{GN}{H2}}$$

using an empirical affine relationship of:

$$\Xi_{\frac{GN}{H2}} = \alpha + \beta \cdot Y + \gamma \cdot X_{H_2}$$

where:
- $\alpha$, $\beta$, and $\gamma$ are coefficients predetermined for the family of fuel gases; and
- Y is a variable representative of physical properties of the fuel gas prepared from the measurements of the at least two flow properties of the fuel gas, the physical properties of the fuel gas comprising at least one of: a viscosity, a specific heat capacity, or a density of the fuel gas.

13. The device according to claim 12, wherein:
the at least one combustion characteristic of the fuel gas comprises the Wobbe index $$IW_{\frac{GN}{H2}}:[[,]]$$

the device further comprises:
- a first inlet configured to receive a stream of the fuel gas;
- a second inlet configured to receive a stream of a reference gas;
- at least one valve configured to deliver the stream of the fuel gas or the stream of the reference gas to a pipe;
- a fluid flow constriction; and
- at least one third sensor configured to measure (i) a mass flow rate of the fuel gas in sonic flow through the fluid flow constriction, (ii) an absolute pressure upstream from the constriction, and (iii) an absolute temperature upstream from the constriction; and an empirical affine relationship used for estimating the Wobbe index $$IW_{\frac{GN}{H2}}$$

is expressed as:

$$IW_{\frac{GN}{H2}} = D + E \cdot Y + F \cdot X_{H_2}$$

with:

$$Y = \frac{Q_{mes,2}}{Q_{ref}} \cdot \frac{p_{ref}}{p_{mes}} \cdot \sqrt{\frac{T_{ref}}{T_{mes}}}$$

where:
- $Q_{mes,2}$ is the measured mass flow rate of the fuel gas;
- $p_{mes}$ is the measured absolute pressure of the fuel gas;
- $T_{mes}$ is the measured absolute temperature of the fuel gas;
- $Q_{ref}$ is the measured mass flow rate of the reference gas;
- $p_{ref}$ is the measured absolute pressure of the reference gas;
- $T_{ref}$ is the measured absolute temperature of the reference gas; and
- D, E, and F are predetermined coefficients for the family of fuel gases and correspond respectively to the coefficients $\alpha$, $\beta$, and $\gamma$.

14. The device according to claim 12, wherein:
the device is configured to estimate the Wobbe index of the fuel gas;
the device further comprises a third sensor configured to measure the density of the fuel gas; and
the processor is configured to estimate the higher heating value from the estimated Wobbe index and from the density of the fuel gas.

15. The device according to claim 12, wherein:
the at least one combustion characteristic of the fuel gas comprises the higher heating value $$HHV_{\frac{GN}{H2}};$$

the device further comprises:
- an inlet configured to receive a stream of the fuel gas;
- a third sensor configure to measure a mass flow rate of the fuel gas in laminar flow through an apparatus giving rise to a pressure drop, the measurement depending on the viscosity of the fuel gas and on a viscosity of a reference gas; and
- a thermal mass flow meter, downstream from the apparatus giving rise to the pressure drop, configured to measure the mass flow rate of the fuel gas, the measurement depending on the specific heat capacity of the fuel gas and on a heat capacity of the reference gas; and an empirical affine relationship used for estimating the higher heating value $$HHV_{\frac{GN}{H2}}$$

is expressed as:

$$HHV_{\frac{GN}{H2}} = A + B \cdot Z + C \cdot X_{H_2}$$

with:

$$Z = \frac{Q_{mes,1}}{Q_{mes,2}}$$

where:
- Z is a variable corresponding to the variable Y;
- $Q_{mes,1}$ is the mass flow rate of the fuel gas in laminar flow through the apparatus giving rise to the pressure drop;
- $Q_{mes,2}$ is the mass flow rate of the fuel gas measured downstream from the apparatus giving rise to the pressure drop; and
- A, B, and C are predetermined coefficients for the family of fuel gases and correspond respectively to the coefficients $\alpha$, $\beta$, and $\gamma$.

16. The device according to claim 12, wherein the processor is also configured to estimate a stoichiometric volume of air or a combustibility index.

17. The device according to claim 12, further comprising:
an actuator configured to regulate the at least one combustion characteristic of the fuel gas or to regulate the at least one combustion characteristic of the fuel gas and an estimated stoichiometric volume of air or an estimated combustibility index corresponding to the at least one combustion characteristic.

18. A non-transitory computer-readable medium containing instructions that when executed cause a processor to:
estimate at least one combustion characteristic of a fuel gas belonging to a family of fuel gases, the at least one combustion characteristic comprising at least one of a Wobbe index or a higher heating value;
wherein, to estimate the at least one combustion characteristic of the fuel gas, the instructions when executed cause the processor to:
- obtain measurements of at least two flow properties of the fuel gas, the at least two flow properties comprising two or more of: a flow rate, a temperature, or a pressure;
- obtain a measurement of a dihydrogen content $X_{H_2}$ contained in the fuel gas; and
- estimate the at least one characteristic $$\Xi_{\frac{GN}{H2}}$$

using an empirical affine relationship of:

$$\Xi_{\frac{GN}{H2}} = \alpha + \beta \cdot Y + \gamma \cdot X_{H_2}$$

where:
- $\alpha$, $\beta$, and $\gamma$ are coefficients predetermined for the family of fuel gases; and
- Y is a variable representative of physical properties of the fuel gas prepared from the measurements of the at least two flow properties of the fuel gas, the physical properties of the fuel gas comprising at least one of: a viscosity, a specific heat capacity, or a density of the fuel gas.

19. The non-transitory computer-readable medium of claim 18, wherein:
the at least one combustion characteristic of the fuel gas comprises the Wobbe index $$IW_{\frac{GN}{H2}};$$

the measurements of the at least two flow properties of the fuel gas include a measurement of a mass flow rate of the fuel gas in sonic flow through a fluid flow constriction, the measurement being taken at an absolute pressure measured upstream from the constriction and at an absolute temperature measured upstream from the constriction;

the instructions when executed further cause the processor to perform a calibration procedure during which a measurement is obtained of a mass flow rate of a reference gas in sonic flow through the fluid flow constriction at a measured reference absolute pressure and at a measured reference absolute temperature; and an empirical affine relationship used for estimating the Wobbe index $$IW_{\frac{GN}{H2}}$$

is expressed as:

$$IW_{\frac{GN}{H2}} = D + E \cdot Y + F \cdot X_{H_2}$$

with:

$$Y = \frac{Q_{mes,2}}{Q_{ref}} \cdot \frac{p_{ref}}{p_{mes}} \cdot \sqrt{\frac{T_{ref}}{T_{mes}}}$$

where:

$Q_{mes,2}$ is the measured mass flow rate of the fuel gas;

$p_{mes}$ is the measured absolute pressure of the fuel gas;

$T_{mes}$ is the measured absolute temperature of the fuel gas;

$Q_{ref}$ is the measured mass flow rate of the reference gas;

$p_{ref}$ is the measured absolute pressure of the reference gas;

$T_{ref}$ is the measured absolute temperature of the reference gas; and

D, E, and F are predetermined coefficients for the family of fuel gases and correspond respectively to the coefficients $\alpha$, $\beta$, and $\gamma$.

20. The non-transitory computer-readable medium of claim 18, wherein:

the at least one combustion characteristic of the fuel gas comprises the higher heating value $$HHV_{\frac{GN}{H2}};$$

the measurements of the at least two flow properties of the fuel gas comprise:

a measurement of a mass flow rate of the fuel gas in laminar flow through an apparatus giving rise to a pressure drop, the measurement depending on the viscosity of the fuel gas and on a viscosity of a reference gas; and a measurement, downstream from the apparatus giving rise to the pressure drop, of the mass flow rate of the fuel gas, the measurement depending on the specific heat capacity of the fuel gas and on a heat capacity of the reference gas; and an empirical affine relationship used for estimating the higher heating value $$HHV_{\frac{GN}{H2}}$$

is expressed as:

$$HHV_{\frac{GN}{H2}} = A + B \cdot Z + C \cdot X_{H_2}$$

with:

$$Z = \frac{Q_{mes,1}}{Q_{mes,2}}$$

where:

Z is a variable corresponding to the variable Y;

$Q_{mes,1}$ is the mass flow rate of the fuel gas in laminar flow through the apparatus giving rise to the pressure drop;

$Q_{mes,2}$ is the mass flow rate of the fuel gas measured downstream from the apparatus giving rise to the pressure drop; and A, B, and C are predetermined coefficients for the family of fuel gases and correspond respectively to the coefficients $\alpha$, $\beta$, and $\gamma$.

* * * * *